(12) United States Patent
Tate et al.

(10) Patent No.: US 11,862,316 B2
(45) Date of Patent: *Jan. 2, 2024

(54) ELECTRONIC HEALTH RECORDS CONNECTIVITY

(71) Applicant: CVS Pharmacy, Inc., Woonsocket, RI (US)

(72) Inventors: Bryan D. Tate, Warwick, RI (US); Meghan A. Ziobro, Newport, RI (US); Adam D. Sah, New York, NY (US); Danielle L. Blackman, Natick, MA (US); Prem S. Shah, St. Petersburg, FL (US); Joel P. Helle, Phoenix, AZ (US); Olga L. Korsunsky, Buffalo Grove, IL (US); Daphne Psacharopoulos, Newton, MA (US)

(73) Assignee: CVS Pharmacy, Inc., Woonsocket, RI (US)

(*) Notice: Subject to any disclaimer, the term of this patent is extended or adjusted under 35 U.S.C. 154(b) by 0 days.

This patent is subject to a terminal disclaimer.

(21) Appl. No.: 17/885,043

(22) Filed: Aug. 10, 2022

(65) Prior Publication Data

US 2022/0384008 A1    Dec. 1, 2022

Related U.S. Application Data

(63) Continuation of application No. 16/435,165, filed on Jun. 7, 2019, now Pat. No. 11,417,421.

(60) Provisional application No. 62/682,922, filed on Jun. 9, 2018.

(51) Int. Cl.
    *G16H 20/10* (2018.01)
    *G16H 10/60* (2018.01)

(52) U.S. Cl.
    CPC ............. *G16H 20/10* (2018.01); *G16H 10/60* (2018.01)

(58) Field of Classification Search
    CPC ............................. G16H 10/60; G16H 20/10
    See application file for complete search history.

(56) References Cited

U.S. PATENT DOCUMENTS

| | | |
|---|---|---|
| 8,392,214 B1 | 3/2013 | Pinsonneault |
| 10,296,715 B1 | 5/2019 | Smith et al. |
| 10,423,759 B1 | 9/2019 | Harris, Sr. et al. |
| 10,742,654 B1 | 8/2020 | Pinsonneault et al. |
| 11,417,421 B1* | 8/2022 | Tate ............... G16H 50/20 |
| 2001/0053986 A1* | 12/2001 | Dick ............... G16H 15/00 705/3 |
| 2011/0071847 A1 | 3/2011 | Keresman, III et al. |
| 2011/0257992 A1 | 10/2011 | Scantland et al. |

(Continued)

*Primary Examiner* — Mamon Obeid
*Assistant Examiner* — Chance L Smith
(74) *Attorney, Agent, or Firm* — Patent Law Works, LLP (57) ABSTRACT

A system and method for obtaining prior authorization and fulfilling a prescription is described. The method includes receiving, by a computing device, prescription information for a patient from a prescriber; identifying, by the computing device, an electronic health record associated with the patient; collecting, by the computing device, medical information for the patient related to the prescription from the electronic health record; submitting, by the computing device, a claim for the prescription with a payor associated with the patient; and completing, by the computing device, a prior authorization request for the prescription.

20 Claims, 5 Drawing Sheets

(56) References Cited

U.S. PATENT DOCUMENTS

| | | | |
|---|---|---|---|
| 2015/0112723 A1* | 4/2015 | Holt | G16H 20/10 |
| | | | 705/3 |
| 2015/0254425 A1 | 9/2015 | Pauletto et al. | |
| 2015/0278474 A1 | 10/2015 | Stueckemann et al. | |
| 2015/0324547 A1 | 11/2015 | Graham et al. | |
| 2016/0034668 A1* | 2/2016 | Rourke | G16H 10/60 |
| | | | 705/2 |
| 2017/0046492 A1 | 2/2017 | Renner et al. | |
| 2017/0091416 A1 | 3/2017 | Mink et al. | |
| 2019/0378598 A1 | 12/2019 | Johnson et al. | |

\* cited by examiner

ELECTRONIC HEALTH RECORDS CONNECTIVITY

CROSS REFERENCE TO RELATED APPLICATIONS

The present application is a continuation of U.S. patent application Ser. No. 16/435,165, filed Jun. 7, 2019, titled "Electronic Health Records Connectivity", which claims priority to U.S. Patent Application No. 62/682,922, titled "Electronic Health Records Connectivity," filed Jun. 9, 2018, the entireties of which are incorporated by reference in their entirety.

Applicants hereby notify the USPTO that the claims of the present application are different from those of the parent application and any other related applications. Therefore, Applicants rescind any disclaimer of claim scope made in the parent application or any other predecessor application in relation to the present application. The Examiner is therefore advised that any such disclaimer and the cited reference that it was made to avoid may need to be revisited at this time. Furthermore, the Examiner is also reminded that any disclaimer made in the present application should not be read into or against the parent application or any other related application.

BACKGROUND

Current processes for prescribing a medication (particularly a specialty medication) and the fulfillment of that prescription include many highly manual and inefficient steps. This negatively affects the experience of both medical doctors and their staff (MDOs) as well as their patients. One particular issue with fulfillment of prescribed medications is payor (e.g., insurance company) requirements for prior authorization before fulfilling the prescribed medications. Current procedures for receiving a prior authorization require several communications between MDOs, patients, and payor, manual data gathering, clinical reviews, and data entry steps.

SUMMARY

A system and method for obtaining prior authorization and fulfilling a prescription is described. One general aspect includes a computer-implemented method including: receiving, by a computing device, prescription information associated with a patient; collecting, by the computing device, medical information associated with the patient from an electronic health record of the patient; processing, by the computing device, a claim for the prescription and obtaining prior authorization for the claim; and packaging and delivering, by the computing device, the medication for which the prescription was received. Other embodiments of this aspect include corresponding computer systems, apparatus, and computer programs recorded on one or more computer storage devices, each configured to perform the actions of the methods.

Implementations may include one or more of the following features. The computer-implemented method where identifying the electronic health record associated with the patient includes: identifying, by the computing device, a prescribing institution from which the prescription originated; accessing, by the computing device, an electronic health record system associated with the prescribing institution; and identifying, by the computing device, the electronic health record associated with patient within the electronic health record system. The computer-implemented method where collecting medical information for the patient related to the prescription from the electronic health record includes: using a statistical model, by the computing device, to identify portions of the electronic health record that are relevant to the prescription. The computer-implemented method where the statistical model is developed based on one or more of: prescriber information, prescribing institution information, patient data, patient interactions with the prescriber and/or prescribing institution, information about an electronic health record system associated with a prescribing institution, and historical pharmacy transactions with the prescriber and/or prescribing institution. The computer-implemented method where completing the prior authorization request for the prescription includes: retrieving, by the computing device, a prior authorization question set from the payor; matching, by the computing device, data from the prescription and the electronic health record of the patient to questions in the prior authorization question set; populating, by the computing device, the prior authorization question set with data from the prescription and the electronic health record based on the matching; and submitting, by the computing device, the completed prior authorization question set to the payor. The computer implemented method further including sending, by the computing system, status and/or tracking updates to the patient. The computer-implemented method further including: packaging, by the computing device, the medication for which the prescription was received; and delivering the medication.

Another general aspect includes a system including: one or more processors; and a memory storing instructions that, when executed, cause the one or more processors to: receive prescription information for a patient from a prescriber; identify an electronic health record associated with the patient; collect medical information for the patient related to the prescription from the electronic health record; submit a claim for the prescription with a payor associated with the patient; and complete a prior authorization request for the prescription.

Implementations may include one or more of the following features. The system where to identify the electronic health record associated with the patient, the instructions further cause the one or more processors to: identify a prescribing institution from which the prescription originated; access an electronic health record system associated with the prescribing institution; and identify the electronic health record associated with patient within the electronic health record system. The system where to collect medical information for the patient related to the prescription from the electronic health record, the instructions further cause the one or more processors to use a statistical model to identify portions of the electronic health record that are relevant to the prescription. The system where the statistical model is developed based on one or more of: prescriber information, prescribing institution information, patient data, patient interactions with the prescriber and/or prescribing institution, information about an electronic health record system associated with a prescribing institution, and historical pharmacy transactions with the prescriber and/or prescribing institution. The system where to complete the prior authorization request for the prescription, the instructions further cause the one or more processors to: retrieve a prior authorization question set from the payor; match data from the prescription and the electronic health record of the patient to questions in the prior authorization question set; populate the prior authorization question set with data from the prescription and the electronic health record based on the matching; and submit the completed prior authorization question set to the payor. The system where the instructions further cause the one or more processors to send status and/or tracking updates to the patient. The system where the instructions further cause the one or more processors to: package the medication for which the prescription was received.

Another general aspect includes a computer-implemented method including: receiving, by a computing device, prescription information for a patient from a prescriber; identifying, by the computing device, an electronic health record system associated with the prescriber; identifying, by the computing device, an electronic health record associated with patient within the electronic health record system. collecting, by the computing device, medical information for the patient related to the prescription from the electronic health record; retrieving, by the computing device, a prior authorization question set from the payor; matching, by the computing device, data from the prescription and the electronic health record of the patient to questions in the prior authorization question set; populating, by the computing device, the prior authorization question set with data from the prescription and the electronic health record based on the matching; and submitting, by the computing device, the completed prior authorization question set to the payor. Other embodiments of this aspect include corresponding computer systems, apparatus, and computer programs recorded on one or more computer storage devices, each configured to perform the actions of the methods.

Implementations may include one or more of the following features. The computer-implemented method where collecting medical information for the patient related to the prescription from the electronic health record includes: using a statistical model, by the computing device, to identify portions of the electronic health record that are relevant to the prescription. The computer-implemented method where the statistical model is developed based on one or more of: prescriber information, prescribing institution information, patient data, patient interactions with the prescriber and/or prescribing institution, information about an electronic health record system associated with a prescribing institution, and historical pharmacy transactions with the prescriber and/or prescribing institution. The computer implemented method further including sending, by the computing system, status and/or tracking updates to the patient. The computer-implemented method further including: packaging, by the computing device, the medication for which the prescription was received; and delivering the medication.

It should be understood that the language used in the present disclosure has been principally selected for readability and instructional purposes, and not to limit the scope of the subject matter disclosed herein.

BRIEF DESCRIPTION OF THE DRAWINGS

The present disclosure is illustrated by way of example, and not by way of limitation in the figures of the accompanying drawings in which like reference numerals are used to refer to similar elements.

DETAILED DESCRIPTION

As set forth in detail below, the technology described herein provides an innovative approach to deliver a full-service experience for specialty medications, that relieves MDOs of administrative burden, improves patient delivery timeframes, improves clinical outcomes, and increases patient adherence and satisfaction. For example, the technology described herein provides a connection to an electronic health record associated with a patient which includes information that can be leveraged for identifying benefit information (e.g., insurance carrier, etc.) of the patient and automatically initiating submission of a claim and/or requesting a prior authorization (PA) for payment of the claim and/or facilitating pharmacist clinical review of the relevant patient medical information. The electronic health record system connection allows this to all be done with minimal to no manual intervention by the MDO staff and/or the patient. Additionally, the technology described herein provides for continuous monitoring of the process by the MDO and/or the patient.

With reference to the figures, reference numbers may be used to refer to components found in any of the figures, regardless whether those reference numbers are shown in the figure being described. Further, where a reference number includes a letter referring to one of multiple similar components (e.g., component 000a, 000b, and 000n), the reference number may be used without the letter to refer to one or all of the similar components.

Figure 1:
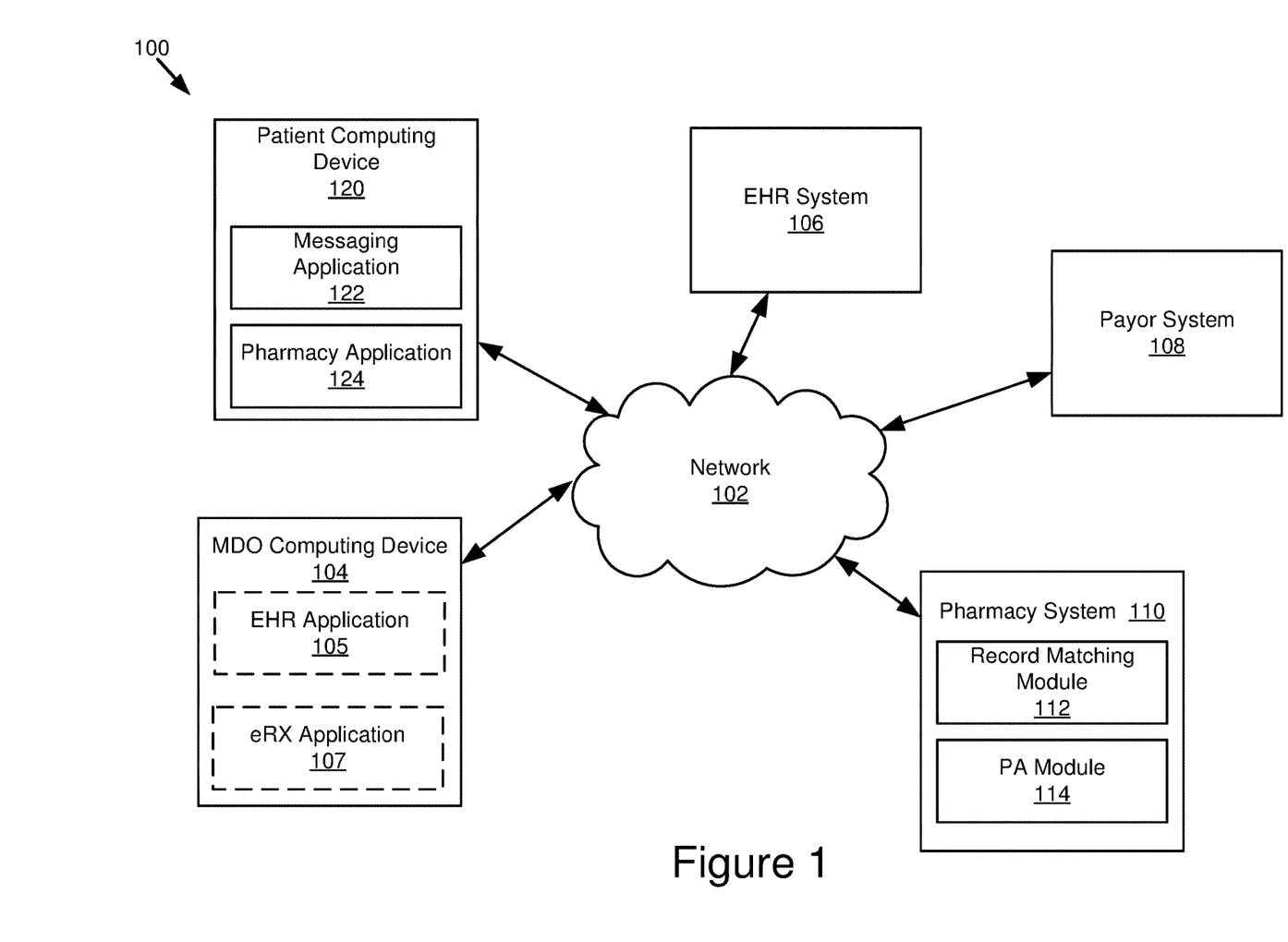
FIG. 1 is a block diagram of an example system for medication prescription fulfillment.

FIG. 1 is a block diagram of an example system 100 for medication prescription fulfillment. The illustrated system 100 may include MDO computing device 104, Electronic Health Record (EHR) system 106, a payor system 108, and a pharmacy system 110, each of which may be electronically communicatively coupled via a network 102 for interaction with one another, although other system configurations are possible including other devices, systems, and networks.

The network 102 may include any number of interoperable networks and/or network types. For example, the network 102 may include, but is not limited to, one or more local area networks (LANs), wide area networks (WANs) (e.g., the Internet), virtual private networks (VPNs), wireless wide area network (WWANs), WiMAX® networks, personal area networks (PANs) (e.g., Bluetooth® communication networks), blockchain-based networks, store-and-forward networks (e.g., SMTP, IMAP, POP, etc.) various combinations thereof, etc. These private and/or public networks may have any number of configurations and/or topologies, and data may be transmitted via the networks using a variety of different communication protocols including, for example, various Internet layer, transport layer, or application layer protocols. For example, data may be transmitted via the networks using TCP/IP, UDP, TCP, HTTP, HTTPS, DASH, RTSP, RTP, RTCP, VOIP, FTP, WS, WAP, SMS, MMS, XMS, IMAP, SMTP, POP, WebDAV, or other known protocols.

The MDO computing device 104 includes one or more computing devices having data processing and communication capabilities. The computing devices may be configured to include an EHR application 105 which provides an interface for MDO staff to view and/or edit information in a patient's electronic health record. Additionally, the MDO computing device may further be configured to include an electronic prescription application 107 which allows the MDO staff to electronically submit prescriptions to a pharmacy for fulfillment.

The EHR system 106 includes one or more computing devices having data processing and communication capabilities. In some embodiments, the EHR system 106 provides electronic health or medical record services to the MDO which can be accessed, for example, via EHR application 105. The EHR system 106 may be located on the premises of the MDO or may be remotely located and accessed via network 102. In some embodiments, a third-party service provider maintains the EHR system 106 and in other embodiments, MDO staff maintain the EHR system 106. EHR is used herein to describe an electronic collection of patient and clinical data and it should be understood that the term EHR may encompass any such electronic health or medical record system.

The electronic health record services may include everything typically found in a paper chart, such as medical history, diagnoses, medications, immunization dates, allergies. The EHR system 106 may be implemented using, for example, Apache cTAKES, AHLTA, athenaClinicals, Centricity EMR, Certify HealthLogix, Cerner EHR, CottageMed, COSTAR, Datix, DocNetwork, Dossia, EMIAS, EMIS Web, EpicCare EMR, FreeMED, GaiaEHR, GNUmed, GPASS, HOSxP, INPS Vision, Kareo EHR, MedcomSoft Record, MTBC WebEHR2.0, NHS Care Records Service, NHS Connecting for Health, OpenEMR, OpenMRS, Practice Fusion, SmartCare, Summary Care Record, TextID, TPP SystmOne, Vetter Software, VistA, VITAband, World Medical Card, ZEPRS, NextGen, eClincalworks, etc.

The payor system 108 includes one or more computing devices having data processing and communication capabilities. In some embodiments, the payor system 108 authorizes payment for patient prescriptions and can provide prior authorization for a prescription. The payor system 108 may be a system implemented by a health insurance provider and/or a pharmacy benefit manager, for example.

The pharmacy system 110 includes one or more computing devices having data processing and communication capabilities. In some embodiments, the pharmacy system 110 provides an interface for pharmacy staff to view and process prescriptions. The pharmacy system 110 is configured to include a record matching module 112 and a prior authorization (PA) module 114. As described in more detail below, the record matching module 112 is configured to retrieve medical records for a patient that are relevant to fulfilling a prescription submitted for the patient. In one embodiment, the PA module 114 is configured to complete a prior authorization request for a prescription received for a patient. In other embodiments, the PA module 114 is configured to provide assistance in completing a prior authorization request for a prescription received for a patient. The function of the PA module 114 is described in more detail below.

The patient computing device 120 may be configured to receive secure and/or unsecure messages via the network 102, receive one or more inputs from a patient, and send a response via the network 102 to the pharmacy system 110 and other components of the system 100. In one embodiment, the patient computing device 120 includes a messaging application 122 and a pharmacy application 124.

In one embodiment, pharmacy application 124 is usable by the patient to fill or refill a prescription and purchase products (e.g., over-the-counter medications, groceries, medical devices, etc.) from a pharmacy. The pharmacy application 124 may further include other tools for tracking medication data associated with the patient (e.g., medication intake, questions regarding a prescription, etc.). The pharmacy application 124 may further be configured to provide for secure communication between a patient and the pharmacy. For example, in one embodiment, a message received by the patient, via the messaging application 122, may include a link that launches the pharmacy application 124 and authenticates the user prior to beginning a secure communication. In another embodiment, the link may launch a web browser on the patient computing device 120 that displays a web page for the pharmacy where the secure communication can take place.

Figure 2:
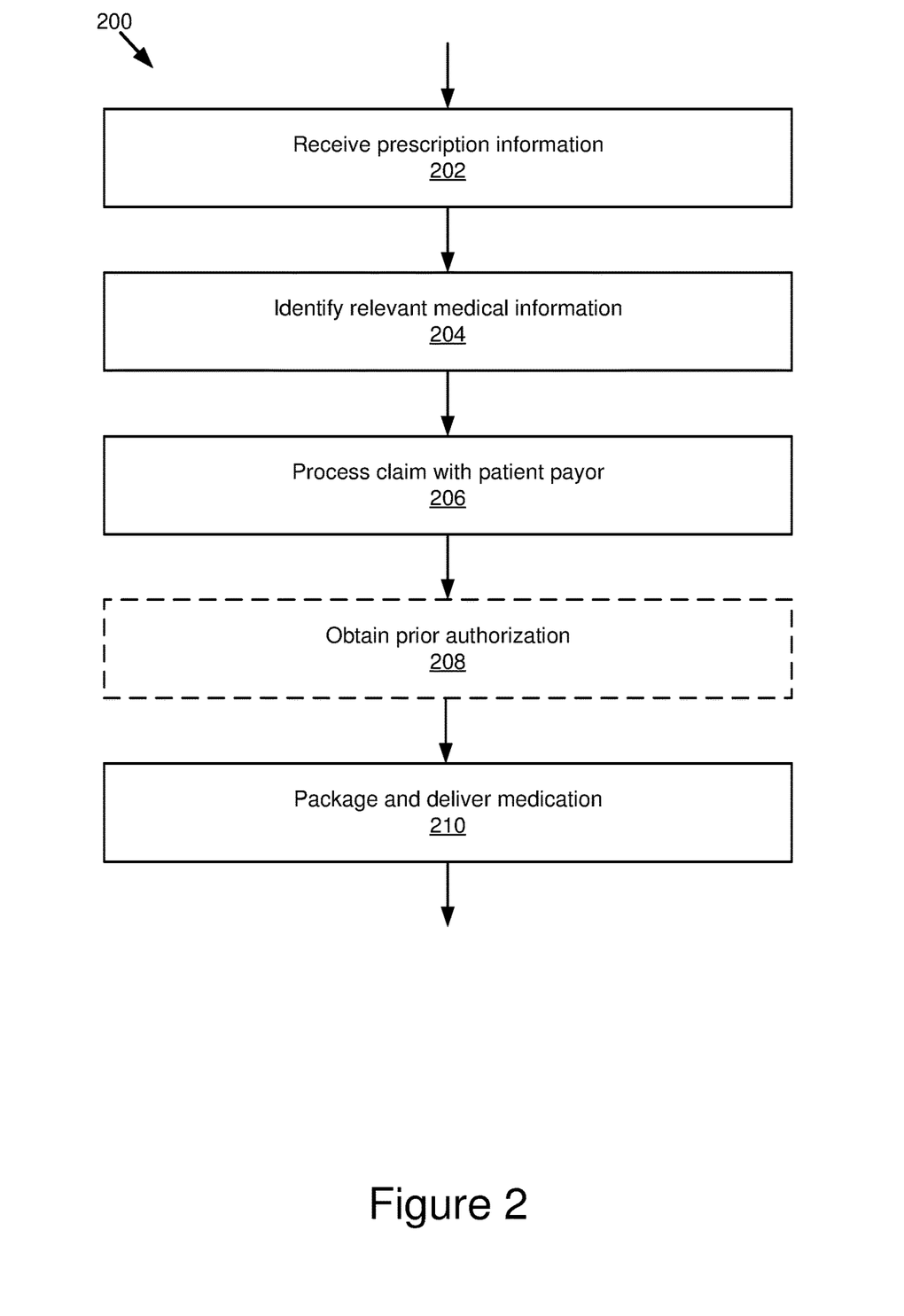
FIG. 2 is a flowchart of an example method for medication prescription fulfillment.

FIG. 2 is a flowchart of an example method 200 for medication prescription fulfillment. At 202, the system receives prescription information. For example, the pharmacy system 110 may receive electronic prescription information from the MDO computing device via network 102. In some embodiments, prior to receiving the prescription information, a patient record may be created for the patient in the EHR system 106. For example, MDO staff may enter patient information into an intake form via eRX application 107. In other embodiments, a patient record already exists in the EHR system 106. In some embodiments, during the initial intake or during a visit with the MDO staff, the patient may opt-in to receive secure communications from the pharmacy system relating to filling and/or refilling of prescriptions from the MDO.

At 204, the pharmacy system 110 identifies relevant medical information for the patient associated with the prescription. In one embodiment, the relevant medical information is included in the patient's electronic health record and is accessed via an integration between the EHR system 106 and the pharmacy system 110 (e.g., via network 102). To ensure compliance with applicable health privacy laws, for example, the record matching module 112 is configured to only retrieve portions of the patient medical record that are relevant to fulfillment of the prescription.

Figure 3:
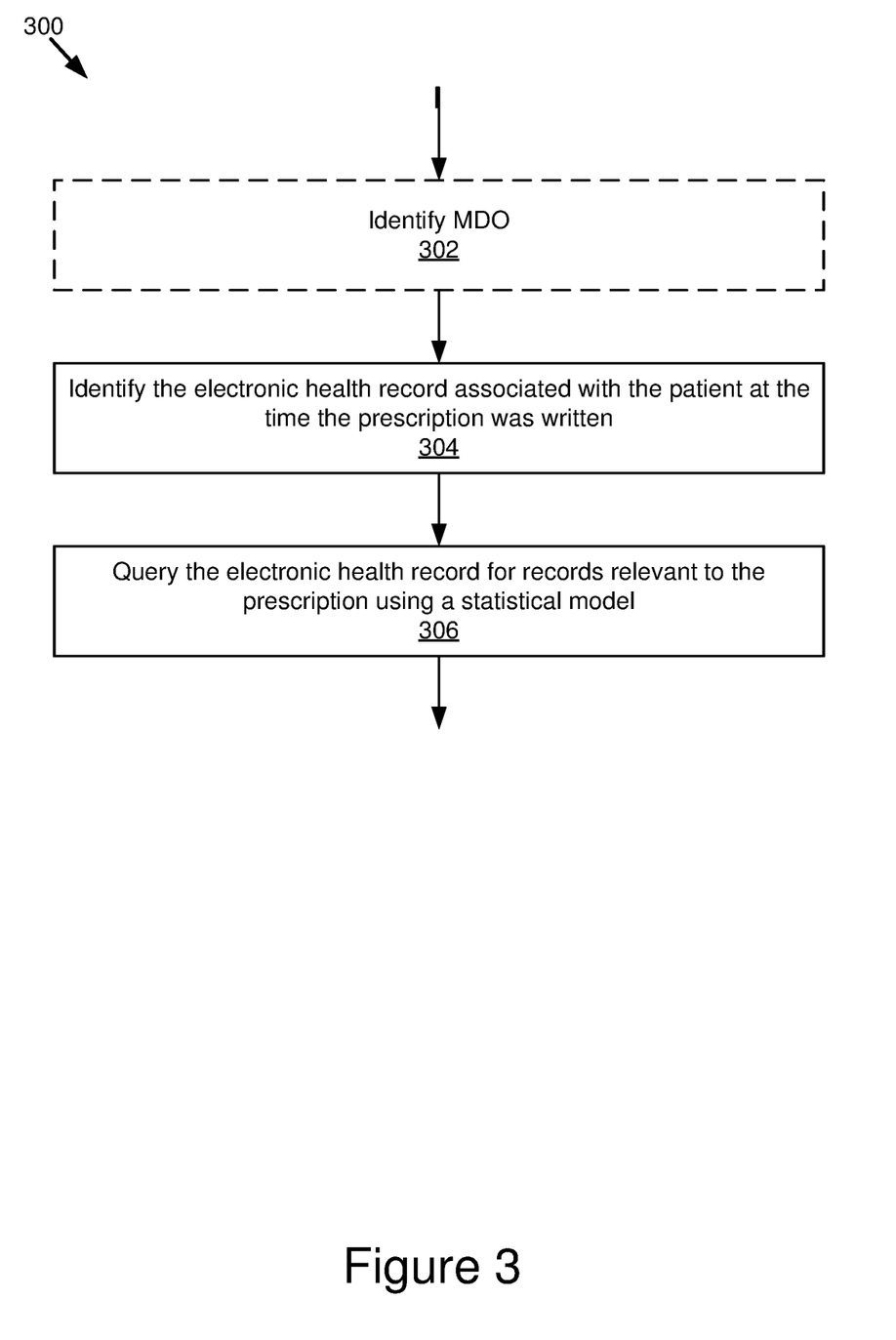
FIG. 3 is a flowchart of an example method for identifying relevant medical information for the patient associated with the prescription.

FIG. 3 is a flowchart of an example method 300 for identifying relevant medical information for the patient associated with the prescription.

In some cases, a unique MDO (e.g., a clinic, hospital, office, etc.) is not provided with the prescription and the record matching module 112, at 302, identifies the MDO from known information. In one method, the record matching module 112 matches data from the prescription against a database of known MDOs to select a specific MDO. For example, in one method, the record matching module 112 may match the MDO with the prescriber using a prescriber identifier number (e.g., a national provider identifier (NPI)).

In other embodiments, the record matching module 112 uses other identifiers and an additional matching process when no prescriber identifier is present (e.g. using prescriber name, geographic location, specialty, type of therapy being prescribed, etc.). For example, the pharmacy computing device 110 may include a database of known MDOs that the given prescriber has historically written prescriptions from and the record matching module 112 may use know information to query the database. If the query returns multiple MDOs, the record matching module 112 may use a ranking function to rank-order the MDOs by the most likely match. In one embodiment, the record matching module 112 may automatically select the top result as being correct, for example, if the number one ranking MDO has a high value substantially larger than the next MDO. In one embodiment, the ranking function may take into account how geographically close the MDO is to a geographical location identified by the prescription (or by another database whose records are looked-up from the fields in the prescription). For example, the geographical location may be identified by a lookup in a known database of street addresses, such as Google Maps or OpenStreetMaps, which accepts as input a human-readable street address and returns a latitude and longitude, from which physical distance is easily computed. This geographical location may be augmented with other data fields found in both prescription and MDO databases (including but not limited to fax numbers, department numbers and suite numbers) which disambiguate between two departments within a medical institution such as hospital. In one embodiment, if the record matching module 112 cannot identify a single MDO with sufficiently high probability, then human intervention may be requested to selects the MDO.

In one embodiment, both these human-selected and machine-selected MDOs are reviewed by machine and human and a determination is made as to the correctness of the selection. These correct or not-correct determinations may then be used to train a machine learning algorithm, which provides a ranking value for each possible MDO match. In one embodiment, these machine learning-based values may be combined with the other ranking values to determine a confidence score for the determination.

At 304, the record matching module 112 identifies the electronic medical record associated with the patient at the time that the prescription was written. This ensures the most accurate data concerning the condition related to the prescription is available for use by the pharmacy system 110. In one embodiment, the record matching module 112 connects to the electronic medical record stored by the EHR system 106 to identify the electronic medical record directly. In another embodiment, the record matching module 112 connects to a third-party database or network to identify the medical record. In some embodiments, when the third-party database has retrieved medical records prior to the prescription being written, the record matching module 112 determines whether the record was retrieved within a threshold time of the prescription based on timestamps of the record and the prescription. In other embodiments, where the third-party database contains a record that is not within the time threshold, the record matching module 112 requests an updated copy of the electronic health record (e.g., from EHR system 106).

At 306, the record matching module 112 queries the electronic health record for records that are relevant to the prescription. In one embodiment, the record matching module 112 uses a statistical model to identify the portions of the patient's medical record that are relevant to the prescription being processed. The statistical model takes into account several factors in determining relevance of a medical record. For example, the statistical model takes into account prescriber information, prescribing institution information, patient data, patient interactions with the prescriber and/or prescribing institution, information about the configuration of the electronic health record the medication was prescribed from, and historical pharmacy transactions with the prescriber and/or prescribing institution. In some embodiments, the statistical model applies various weights to the input data based on historic trends.

Returning again to FIG. 2, the pharmacy system 110 attempts to process the claim with the payor system 108, at 206. Before the pharmacy can dispense the prescription, the pharmacy typically ensures that the payor (e.g., a pharmacy benefit manager) will reimburse the cost of the prescription. In some embodiments, the payor may reject a claim for payment and require prior authorization. The conventional prior authorization process is time consuming and typically conducted by phone, fax, email, text message. The techniques introduced herein advantageously provide for a semi- or fully-automated computer process with little or no human interaction, which provides faster turnaround time and less effort by MDOs.

In some embodiments, for example when the payor system requires prior authorization, at 208, the pharmacy system 110 may gather the necessary information for obtaining prior authorization from the patient's EHR and submit the prior authorization request for processing.

Figure 4:
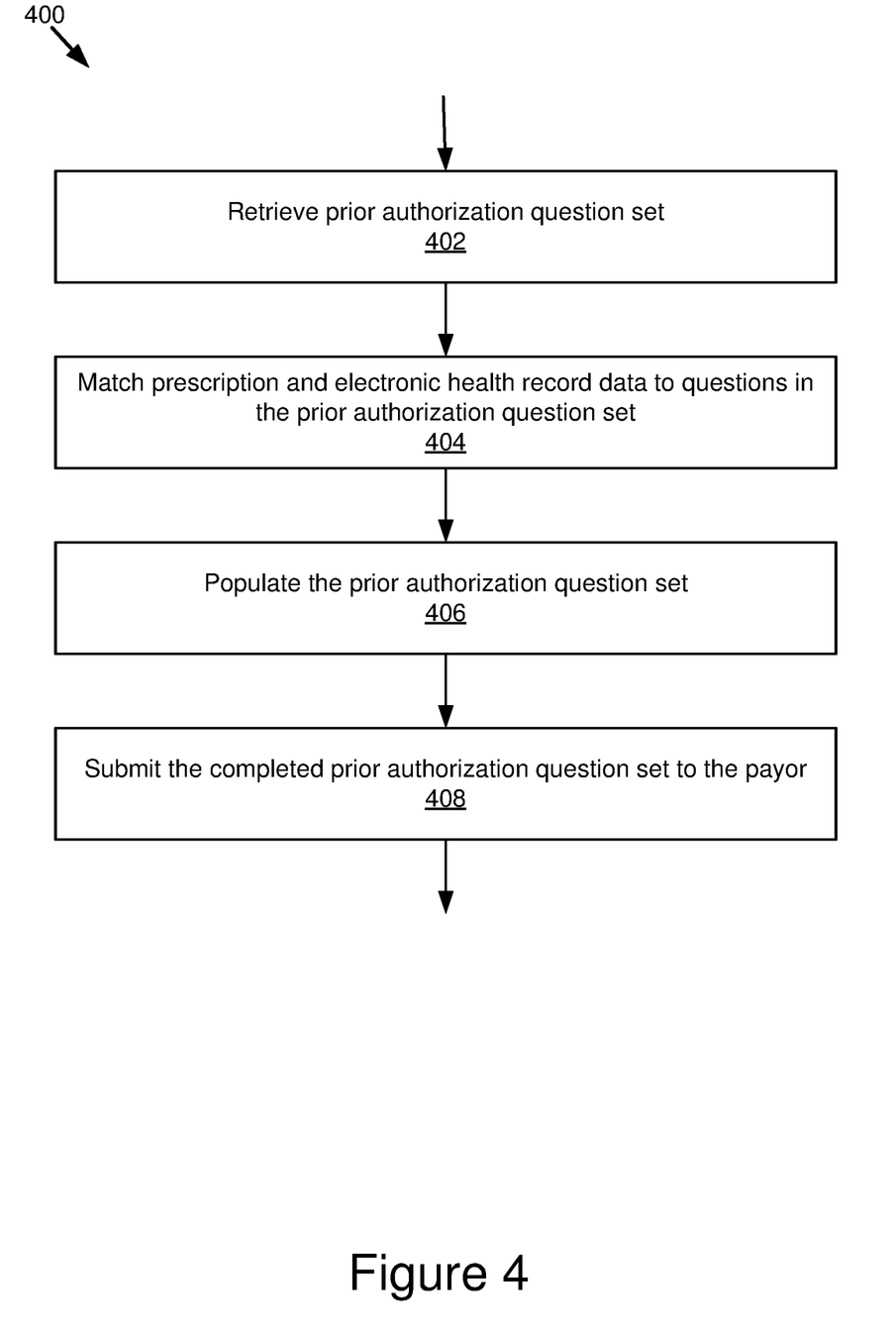
FIG. 4 is a flowchart of an example method for identifying relevant medical information for the patient associated with the prescription.

FIG. 4 is a flowchart of an example method for identifying relevant medical information for the patient associated with the prescription.

At 402, the prior authorization module 114 retrieves a prior authorization question set. In one embodiment, a prior authorization question set is received from the payor system 108 when a payment claim for the prescription is denied. In another embodiment, the pharmacy system 110 includes a database of prior authorization question sets from various payors and the prior authorization module 114 retrieves the relevant prior authorization question set from the database.

At 404, the prior authorization module 114 matches prescription and electronic health record data to questions in the prior authorization question set. In one embodiment, the prior authorization module 114 parses each question from the prior authorization question set document. In one embodiment, this parsing is performed by "scraping" techniques that look for markers in the text (e.g., numerals) and then capture the question near that marker. In another embodiment, natural language processing (NLP) techniques are used to identify the question text and related contextual information. In yet another embodiment, a machine learning algorithm is trained, using previously parsed prior authorization question sets, to automatically segment the questions.

After the questions have been parsed, the prior authorization module determines the content of the question. In one embodiment, a set of question "types" is established, for example, questions relating to prior treatments, questions relating to side effects, questions relating to whether diagnostic tests have been performed or their results, etc. The prior authorization module 114 may then map or tag the questions of the prior authorization question set with an associated question type(s) via explicit pattern match, NLP, or a machine learning algorithm.

In another embodiment, human intervention may be used to match data from the prescription and or electronic health record to a prior authorization question. In one embodiment a graphical user interface may be displayed to the human user with the prior authorization question in one pane and the prescription and relevant electronic health record information in another pane. The user may then copy and paste or drag and drop the data from the prescription and/or electronic health record to the prior authorization question or vice versa. This human matching may be stored in a database and used for later training of a machine learning algorithm as discussed elsewhere herein.

Often, prior authorization question sets may include "dependent" questions that are only required if a prior question was answered a certain way. In some embodiments, the prior authorization module 114 matches questions (particularly dependent questions) to data from the prescription and/or electronic health record based on pattern matching.

In some embodiments, the prior authorization module 114 engages the prescriber and/or patient to gather additional data and/or confirm information that is possibly inconsistent or is associated with a high risk of prior authorization rejection. Interaction with a patient may take place via the messaging application 122 or pharmacy application 124 of the patient computing device 120 and interaction with a prescriber may take place via the electronic prescription application 107 or other communication mechanism of the MDO computing device 104. It should be apparent that other communication means may be used.

To determine whether to engage with a prescriber and/or patient, the prior authorization module 114 scans the prior authorization question set and constructs a score for each question for prescriber engagement and a separate score for patient engagement. The prior authorization module 114 may then compare the scores to a threshold and engage with the prescriber and/or patient based on the comparison. In one embodiment, the prior authorization module 114 scans the prior authorization question and uses a machine learning algorithm to detect the value of engagement. The machine learning algorithm may be trained using prior engagements and lack of engagements, with additional inputs from subjective feedback from the humans as well as the outcome of prior authorization request (e.g., acceptance, rejection, appeal).

At 406, the prior authorization module 114 populates the prior authorization question set. Given the prescription, the relevant electronic health record data, and the matched prior authorization questions, the prior authorization module 114 can begin to automatically respond to the payor without manual intervention from the prescriber or patient. This advantageously accelerates the prior authorization process and ultimately the delivery of the medication to the patient. For example, if the prior authorization module 114 can fully complete the response to the prior authorization question set, the response can be provided to the payor in seconds rather than the typical days of delay caused by the conventional process.

In one embodiment, inserting data from the prescription and electronic health record in the prior authorization question set is performed automatically by the prior authorization module 114. In another embodiment, inserting data from the prescription and electronic health record in the prior authorization question set is performed by a human who is assisted by the prior authorization module 114 which suggests inputs to consider and/or provides user interfaces which accelerate the completion process (e.g. auto-complete).

In one embodiment, the prior authorization module 114 uses type tags complete the form by inserting data from the prescription and/or medical record that corresponds to the type tag associated with a prior authorization question.

In one embodiment, prior authorization module 114 fills out the prior authorization question set ignoring dependencies, i.e. always attempt to answer every question. In another embodiment, the prior authorization module 114 detects dependent questions and answer "n/a" (not applicable) if the instructions request that the question be skipped based on a previous answer. In particular, skipping can save time when a question requiring human intervention does not need an answer. In one method, the prior authorization module 114 includes a set of rules that indicate whether a question applies based on previous responses. In embodiment, the rules are human generated (e.g., by a programmer or a programmatic interface). In another embodiment, relevance of a question is determined by a machine learning algorithm trained using prior responses to the same/similar questions.

In one embodiment, data from the prescription and electronic health record may be combined together prior to insertion into the response to the prior authorization question set. In another embodiment, the data from the prescription and electronic health record may be augmented with external data. In another embodiment, the data from the prescription and electronic health record is algorithmically modified prior to insertion into the response to the prior authorization question set. For example, the algorithm may convert codes, numbers, shorthand and values into human-readable language, or vice versa. In some embodiments, the prior authorization module 114 may perform a per-field transformation. For example, the prior authorization module 114 may transform measurement units. The prior authorization module 114 may also parse the original data for keywords and construct a grammatically correct sentence in the particular format preferred by the given payor. It should be noted that the source data may be multiple fields from multiple sources, and in some embodiments the prior authorization module 114 generates a single answer to a single question from the various fields.

In some embodiments, a human might review the completed prior authorization question set. Particularly, the prior authorization module 114 may provide a confidence score for the answers provided and request human review for questions that are below a threshold confidence score. In this way, the techniques described herein help to automate the prior authorization process without unnecessary risk. In one embodiment, the confidence score is presented as a number. In another embodiment, the confidence score may be presented graphically via a user interface of the pharmacy system 110. For example, the confidence score may be represented as a color (e.g. green is confident, yellow requires review and red is a wild guess).

To optimize cost and/or turnaround time, the techniques described herein reduce the risk of the completed prior authorization request being rejected once submitted to the payor. This may be accomplished by assigning a holistic "risk" score to the completed prior authorization request using data from prior request submissions, acceptances, rejections and appeals. In one embodiment, this risk score is computed by an algorithm, which takes into account the presence of high-risk questions or high-risk answers. In another embodiment, this risk score is determined by human reviewers. In yet another embodiment, a machine learning algorithm looks at all keywords/phrases in the completed prior authorization request and associates the keywords with acceptance, rejection and appeal to determine a risk score. In another embodiment, a machine generated risk score and a self-confidence score may be blended with a human generated risk assessment score to produce a final risk score used to determine whether to use human review.

In one embodiment, high-risk prior authorization requests (e.g., requests that have a risk score above a threshold) are reviewed by humans prior to being submitted to the payor. In another embodiment, prior authorization requests are randomly reviewed, but higher risk prior authorization requests are more likely to be reviewed by humans than lower risk prior authorization requests based on score weighting. Additionally, all prior authorization requests may be tracked for whether they were accepted or rejected, and this is taken as input to a machine learning algorithm which identifies which fields, values and changes are indicative of a risk for rejection.

At 408, the prior authorization module 114 submits the completed prior authorization question set to the payor.

Returning again to FIG. 2, at 210, the pharmacy system 110 may package and deliver the medication to the patient. In some embodiments, the pharmacy system 110 may communicate status and medication tracking updates to the patient via patient computing device 120. For example, when a prescription is entered into the eRX application 107 and received by the pharmacy system 110, the pharmacy system 110 may send a message to the patient computing device 120 indicating that a prescription has been received by the pharmacy and providing an opportunity for the patient to interact with the pharmacy. The pharmacy system 110 may continue to provide updates to the patient throughout the process. For example, the pharmacy system 110 may send a message when the prescription is ready to ship or is ready for pickup at a retail pharmacy location. Additionally, the pharmacy system 110 may send a message when the prescription has been shipped and provide tracking information for the package.

In some embodiments, as described elsewhere herein, during the fulfillment process, the pharmacy system 110 may communicate with the patient via secure messages to gather additional information needed to fulfill the prescription order (e.g., information needed to submit a prior authorization request).

In some embodiments, during the prescription fulfillment process, the pharmacy system 110 may similarly communicate with the MDO regarding status of the prescription. For example, the pharmacy system 110 may send messages to the MDO via eRX application 107. Additionally, as discussed herein, the pharmacy system 110 may request additional information from the MDO for additional information during the fulfillment process (e.g., lab results for a prior authorization request, etc.)

While the example of FIGS. 2-4 above describes a process and system for automating a prior authorization request within a prescription fulfillment process, it should be understood that the prior authorization request process may be performed independently from the prescription fulfillment process. For example, the record matching module 112 and the prior authorization module 114 may be implemented by MDO computing device 104 and steps 204-208 may be performed by the MDO computing device 104 prior to transmitting the prescription information to the pharmacy system 110. Similarly, the record matching module 112 and the prior authorization module 114 may be implemented by the EHR system 106, the payor system 108, the patient computing device 120, or any other computing system coupled with network 102 and configured to communicate with MDO computing device 104 and/or eRX application 107.

Figure 5:
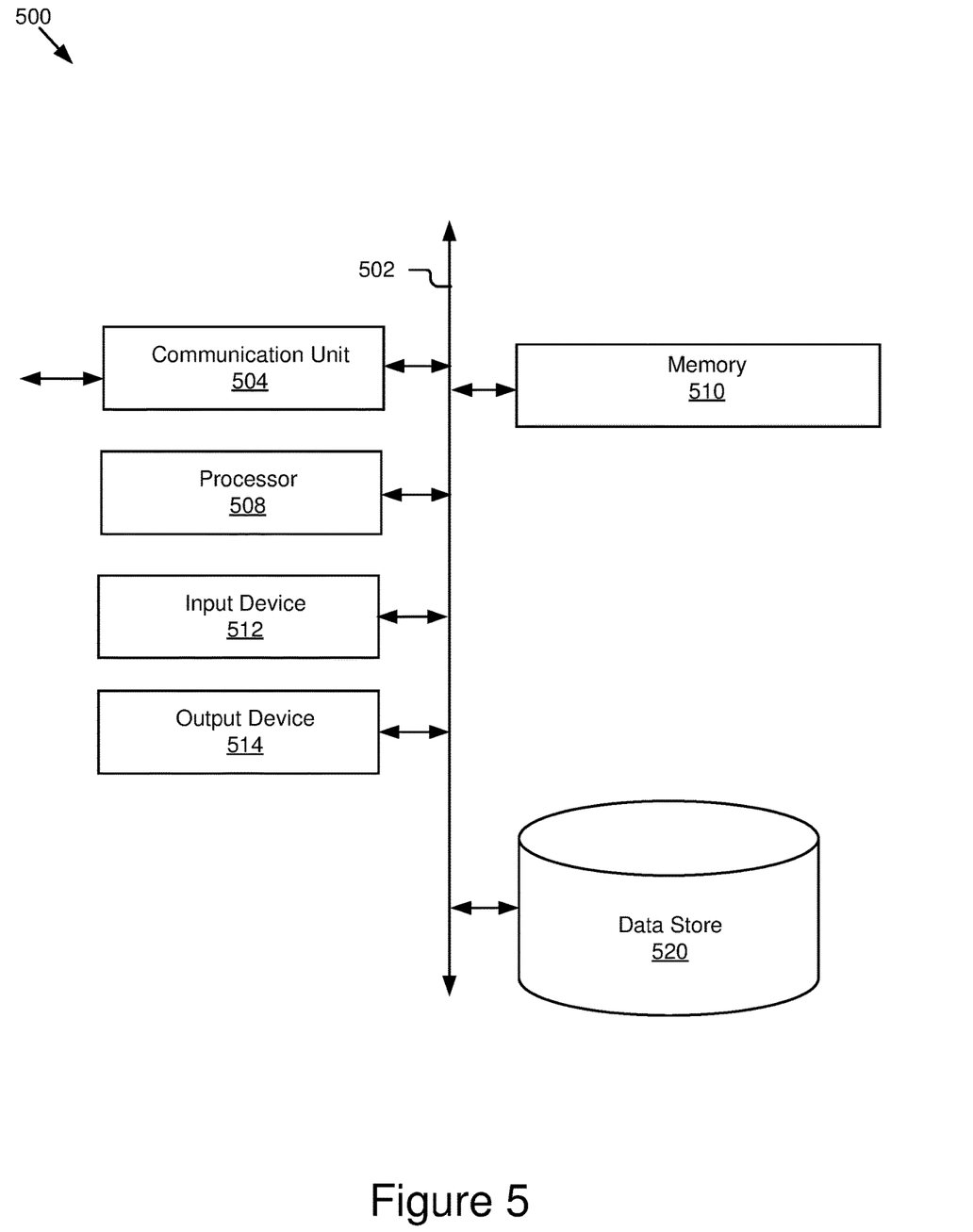
FIG. 5 is a block diagram of an example computing system.

FIG. 5 is a block diagram of an example computing device 500, which may represent a computing device configured to implement modules depicted in FIG. 1, depending on the implementation. For example, the computing system 500 may be used to implement the MDO computing device 104, the EHR system 106, the payor system 108, the pharmacy system 110, and/or the patient computing device 112.

As depicted, the computing system 500 may include a processor 508, a memory 510, a communication unit 504, an output device 514, an input device 512, and a data store 520, which may be communicatively coupled by a communication bus 502. The computing system 500 depicted in FIG. 5 is provided by way of example and it should be understood that it may take other forms and include additional or fewer components without departing from the scope of the present disclosure. For instance, various components of the computing device may be coupled for communication using a variety of communication protocols and/or technologies including, for instance, communication buses, software communication mechanisms, computer networks, etc. While not shown, the computing system 500 may include various operating systems, sensors, additional processors, and other physical configurations. The processor 508, memory 510, communication unit 504, etc., are representative of one or more of these components.

The processor 508 may execute software instructions by performing various input, logical, and/or mathematical operations. The processor 508 may have various computing architectures to method data signals (e.g., CISC, RISC, etc.). The processor 508 may be physical and/or virtual, and may include a single core or plurality of processing units and/or cores. In some implementations, the processor 508 may be coupled to the memory 510 via the bus 502 to access data and instructions therefrom and store data therein. The bus 502 may couple the processor 508 to the other components of the computing system 500 including, for example, the memory 510, the communication unit 504, the input device 512, the output device 514, and the data store 520.

The memory 510 may store and provide data access to the other components of the computing system 500. The memory 510 may be included in a single computing device or a plurality of computing devices. In some implementations, the memory 510 may store instructions and/or data that may be executed by the processor 508. For example, the memory 510 may store instructions and data, including, for example, an operating system, hardware drivers, other software applications, databases, etc. which may implement the techniques described herein. The memory 510 may be coupled to the bus 502 for communication with the processor 508 and the other components of computing system 500.

The memory 510 may include a non-transitory computer-usable (e.g., readable, writeable, etc.) medium, which can be any non-transitory apparatus or device that can contain, store, communicate, propagate or transport instructions, data, computer programs, software, code, routines, etc., for processing by or in connection with the processor 508. In some implementations, the memory 510 may include one or more of volatile memory and non-volatile memory (e.g., RAM, ROM, hard disk, solid-state drive, optical disk, etc.). It should be understood that the memory 510 may be a single device or may include multiple types of devices and configurations.

The bus 502 can include a communication bus for transferring data between components of a computing device or between computing devices, a network bus system including the network 102 or portions thereof, a processor mesh, a combination thereof, etc. In some implementations, various components operating on the computing device 500 (operating systems, device drivers, etc.) may cooperate and communicate via a communication mechanism included in or implemented in association with the bus 502. The software communication mechanism can include and/or facilitate, for example, inter-method communication, local function or procedure calls, remote procedure calls, an object broker (e.g., CORBA), direct socket communication (e.g., TCP/IP sockets) among software modules, UDP broadcasts and receipts, HTTP connections, etc. Further, any or all of the communication could be secure (e.g., SSH, HTTPS, etc.).

The communication unit 504 may include one or more interface devices (I/F) for wired and wireless connectivity among the components of the system 100. For instance, the communication unit 504 may include, but is not limited to, various types of known connectivity and interface options. The communication unit 504 may be coupled to the other components of the computing system 500 via the bus 502. The communication unit 504 can provide other connections to the network 102 and to other entities of the system 100 using various standard communication protocols.

The input device 512 may include any device for inputting information into the computing system 500. In some implementations, the input device 512 may include one or more peripheral devices. For example, the input device 512 may include a keyboard, a pointing device, microphone, an image/video capture device (e.g., camera), a touch-screen display integrated with the output device 514, etc. The output device 514 may be any device capable of outputting information from the computing system 500. The output device 514 may include one or more of a display (LCD, OLED, etc.), a printer, a haptic device, audio reproduction device, touch-screen display, a remote computing device, etc. In some implementations, the output device is a display which may display electronic images and data output by a processor of the computing system 500 for presentation to a user, such as the processor 508 or another dedicated processor.

The data store 520 may include information sources for storing and providing access to data. In some implementations, the data store 520 may store data associated with a database management system (DBMS) operable on the computing system 500. For example, the DBMS could include a structured query language (SQL) DBMS, a NoSQL DBMS, various combinations thereof, etc. In some instances, the DBMS may store data in multi-dimensional tables comprised of rows and columns, and manipulate, e.g., insert, query, update and/or delete, rows of data using programmatic operations.

The data stored by the data store 520 may be organized and queried using various criteria including any type of data stored by them. The data store 520 may include data tables, databases, or other organized collections of data.

The data store 520 may be included in the computing system 500 or in another computing system and/or storage system distinct from but coupled to or accessible by the computing system 500. The data stores 520 can include one or more non-transitory computer-readable mediums for storing the data. In some implementations, the data stores 520 may be incorporated with the memory 510 or may be distinct therefrom.

The components 504, 508, 510, 512, and/or 514 may be communicatively coupled by the bus 502 and/or the processor 508 to one another and/or the other components of the computing system 500. In some implementations, the components 504, 508, 510, 512, and/or 514 may include computer logic (e.g., software logic, hardware logic, etc.) executable by the processor 508 to provide their acts and/or functionality. In any of the foregoing implementations, these components 504, 508, 510, 512, and/or 514 may be adapted for cooperation and communication with the processor 508 and the other components of the computing system 500.

In the above description, for purposes of explanation, numerous specific details are set forth in order to provide a thorough understanding of the present disclosure. However, it should be understood that the technology described herein can be practiced without these specific details. Further, various systems, devices, and structures are shown in block diagram form in order to avoid obscuring the description. For instance, various implementations are described as having particular hardware, software, and user interfaces. However, the present disclosure applies to any type of computing device that can receive data and commands, and to any peripheral devices providing services.

In some instances, various implementations may be presented herein in terms of algorithms and symbolic representations of operations on data bits within a computer memory. An algorithm is here, and generally, conceived to be a self-consistent set of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

To ease description, some elements of the system and/or the methods are referred to using the labels first, second, third, etc. These labels are intended to help to distinguish the elements but do not necessarily imply any particular order or ranking unless indicated otherwise.

It should be borne in mind, however, that all of these and similar terms are to be associated with the appropriate physical quantities and are merely convenient labels applied to these quantities. Unless specifically stated otherwise as apparent from the following discussion, it is appreciated that throughout this disclosure, discussions utilizing terms including "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Various implementations described herein may relate to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, including, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

The technology described herein can take the form of an entirely hardware implementation, an entirely software implementation, or implementations containing both hardware and software elements. For instance, the technology may be implemented in software, which includes but is not limited to firmware, resident software, microcode, etc. Furthermore, the technology can take the form of a computer program object accessible from a computer-usable or computer-readable medium providing program code for use by or in connection with a computer or any instruction execution system. For the purposes of this description, a computer-usable or computer readable medium can be any non-transitory storage apparatus that can contain, store, communicate, propagate, or transport the program for use by or in connection with the instruction execution system, apparatus, or device.

A data processing system suitable for storing and/or executing program code may include at least one processor coupled directly or indirectly to memory elements through a system bus. The memory elements can include local memory employed during actual execution of the program code, bulk storage, and cache memories that provide temporary storage of at least some program code in order to reduce the number of times code must be retrieved from bulk storage during execution. Input or I/O devices (including but not limited to keyboards, displays, pointing devices, etc.) can be coupled to the system either directly or through intervening I/O controllers.

Network adapters may also be coupled to the system to enable the data processing system to become coupled to other data processing systems, storage devices, remote printers, etc., through intervening private and/or public networks. Wireless (e.g., Wi-Fi™) transceivers, Ethernet adapters, and Modems, are just a few examples of network adapters. The private and public networks may have any number of configurations and/or topologies. Data may be transmitted between these devices via the networks using a variety of different communication protocols including, for example, various Internet layer, transport layer, or application layer protocols. For example, data may be transmitted via the networks using transmission control protocol/Internet protocol (TCP/IP), user datagram protocol (UDP), transmission control protocol (TCP), hypertext transfer protocol (HTTP), secure hypertext transfer protocol (HTTPS), dynamic adaptive streaming over HTTP (DASH), real-time streaming protocol (RTSP), real-time transport protocol (RTP) and the real-time transport control protocol (RTCP), voice over Internet protocol (VOIP), file transfer protocol (FTP), WebSocket (WS), wireless access protocol (WAP), various messaging protocols (SMS, MMS, XMS, IMAP, SMTP, POP, WebDAV, etc.), or other known protocols.

Finally, the structure, algorithms, and/or interfaces presented herein are not inherently related to any particular computer or other apparatus. Various general-purpose systems may be used with programs in accordance with the teachings herein, or it may prove convenient to construct more specialized apparatus to perform the required method blocks. The required structure for a variety of these systems will appear from the description above. In addition, the specification is not described with reference to any particular programming language. It will be appreciated that a variety of programming languages may be used to implement the teachings of the specification as described herein.

The foregoing description has been presented for the purposes of illustration and description. It is not intended to be exhaustive or to limit the specification to the precise form disclosed. Many modifications and variations are possible in light of the above teaching. As will be understood by those familiar with the art, the specification may be embodied in other specific forms without departing from the spirit or essential characteristics thereof. Likewise, the particular naming and division of the modules, routines, features, attributes, methodologies and other aspects are not mandatory or significant, and the mechanisms that implement the specification or its features may have different names, divisions and/or formats. Furthermore, the modules, routines, features, attributes, methodologies and other aspects of the disclosure can be implemented as software, hardware, firmware, or any combination of the foregoing. Also, wherever a component, an example of which is a module, of the specification is implemented as software, the component can be implemented as a standalone program, as part of a larger program, as a plurality of separate programs, as a statically or dynamically linked library, as a kernel loadable module, as a device driver, and/or in every and any other way known now or in the future. Additionally, the disclosure is in no way limited to implementation in any specific programming language, or for any specific operating system or environment.

What is claimed is:

1. A computer-implemented method comprising:
    training, using one or more processors, a record matching model to select a medical doctor's office associated with a received prescription, the record matching model providing a ranking value to one or more potential medical doctor's offices associated with the received prescription and selecting an associated medical doctor's office, the associated medical doctor's office associated with the received prescription based on the ranking value;
    receiving, using the one or more processors, a set of selected medical doctor's offices including a first selected medical doctor's office selected, by the record matching model, for association with a first received prescription;
    determining, using the one or more processors, whether the first selected medical doctor's office from the set of selected medical doctor's offices is correct or incorrect;
    retraining, using the one or more processors, the record matching model based on the determination of whether the first selected medical doctor's office from the set of selected medical doctor's offices is correct or incorrect;
    receiving, using the one or more processors, a second prescription for a patient from a prescriber;
    selecting, using the record matching model subsequent to the retraining of the record matching model, a second medical doctor's office associated with the prescriber of the second prescription;
    collecting, using the one or more processors and based on the selection of the second medical doctor's office using the record matching model, a relevant portion of medical information of an electronic health record associated with the second medical doctor's office, the relevant portion of the medical information associated with fulfillment of the second prescription for the patient; and
    submitting, using the one or more processors, the claim for the second prescription.

2. The computer-implemented method of claim 1 further comprising:
    receiving, in response to the claim, a denial of the claim;
    subsequent to receiving the denial of the claim, retrieving a prior authorization question set from a payor; and
    completing a prior authorization request for the second prescription including the prior authorization question set using the relevant portion of the medical information of the electronic health record.

3. The computer-implemented method of claim 2, wherein completing the prior authorization request for the second prescription comprises:
    retrieving a prior authorization question set from a payor;
    matching data from the second prescription and the electronic health record of the patient to questions in the prior authorization question set;
    populating the prior authorization question set with the data from the second prescription and the electronic health record based on the matching; and
    submitting a completed prior authorization question set to the payor.

4. The computer-implemented method of claim 1, wherein the relevant portion of the medical information of the electronic health record is identified prior to submission of the claim and prior to retrieving a prior authorization question set from a payor.

5. The computer-implemented method of claim 1, wherein identifying the electronic health record associated with the patient comprises:
identifying a prescribing institution from which the second prescription originated;
accessing an electronic health record system associated with the prescribing institution; and
identifying the electronic health record associated with patient within the electronic health record system.

6. The computer-implemented method of claim 1, wherein collecting the relevant portion of the medical information comprises:
using a statistical model to identify portions of the electronic health record that are relevant to the second prescription.

7. The computer-implemented method of claim 6, wherein the statistical model is developed based on one or more of: prescriber information, prescribing institution information, patient data, patient interactions with the prescriber, patient interactions with the prescribing institution, information about an electronic health record system associated with a prescribing institution, and historical pharmacy transactions with the prescriber, and historical pharmacy transactions with the prescribing institution.

8. The computer-implemented method of claim 1, further comprising sending one or more of a status update and a tracking update to the patient.

9. The computer-implemented method of claim 1, further comprising:
packaging medication for which the second prescription was received; and
delivering the medication.

10. The computer-implemented method of claim 9, wherein the packaging of the medication for which the second prescription was received is in response to completion of a prior authorization request for the second prescription.

11. A system comprising:
one or more processors; and
a memory storing instructions that, when executed, cause the one or more processors to:
train a record matching model to select a medical doctor's office associated with a received prescription, the record matching model providing a ranking value to one or more potential medical doctor's offices associated with the received prescription and selecting an associated medical doctor's office, the associated medical doctor's office associated with the received prescription based on the ranking value;
receive a set of selected medical doctor's offices including a first selected medical doctor's office selected, by the record matching model, for association with a first received prescription;
determine whether the first selected medical doctor's office from the set of selected medical doctor's offices is correct or incorrect;
retrain the record matching model based on the determination of whether the first selected medical doctor's office from the set of selected medical doctor's offices is correct or incorrect;
receive a second prescription for a patient from a prescriber;
select, using the record matching model subsequent to the retraining of the record matching model, a second medical doctor's office associated with the prescriber of the second prescription;
collect, based on the selection of the second medical doctor's office using the record matching model, a relevant portion of medical information of an electronic health record associated with the second medical doctor's office, the relevant portion of the medical information associated with fulfillment of the second prescription for the patient; and
submit the claim for the second prescription.

12. The system of claim 11, wherein to identify the electronic health record associated with the patient, the instructions further cause the one or more processors to:
receive, in response to the claim, a denial of the claim;
subsequent to receiving the denial of the claim, retrieve a prior authorization question set from a payor; and
complete a prior authorization request for the second prescription including the prior authorization question set using the relevant portion of the medical information of the electronic health record.

13. The system of claim 12, wherein to complete the prior authorization request for the second prescription, the instructions further cause the one or more processors to:
retrieve a prior authorization question set from a payor;
match data from the second prescription and the electronic health record of the patient to questions in the prior authorization question set;
populate the prior authorization question set with the data from the second prescription and the electronic health record based on the matching; and
submit a completed prior authorization question set to the payor.

14. The system of claim 11, wherein the relevant portion of the medical information of the electronic health record is identified prior to submission of the claim and prior to retrieving a prior authorization question set from a payor.

15. The system of claim 11, wherein to identify the electronic health record associated with the patient, the instructions further cause to one or more processors to:
identify a prescribing institution from which the second prescription originated;
access an electronic health record system associated with the prescribing institution; and
identify the electronic health record associated with patient within the electronic health record system.

16. The system of claim 11, wherein to collect the relevant portion of the medical information, the instructions further cause to one or more processors to:
use a statistical model to identify portions of the electronic health record that are relevant to the second prescription.

17. The system of claim 16, wherein the statistical model is developed based on one or more of: prescriber information, prescribing institution information, patient data, patient interactions with the prescriber, patient interactions with the prescribing institution, information about an electronic health record system associated with a prescribing institution, historical pharmacy transactions with the prescriber, and historical pharmacy transactions with the prescribing institution.

18. The system of claim 11, wherein the instructions further cause the one or more processors to send one or more of a status update and a tracking update to the patient.

19. The system of claim 11, wherein the instructions further cause the one or more processors to:

package medication for which the second prescription was received; and deliver the medication.

20. The system of claim 19, wherein the packaging of the medication for which the second prescription was received is in response to completion of a prior authorization request for the second prescription.

\* \* \* \* \*